United States Patent
Schwarz, Jr. et al.

(10) Patent No.: US 11,517,641 B1
(45) Date of Patent: Dec. 6, 2022

(54) SYSTEMS AND METHODS FOR PROVIDING SANITARY TOUCH INTERFACE EXPERIENCES

(71) Applicant: UIPCO, LLC, San Antonio, TX (US)

(72) Inventors: Thomas Wayne Schwarz, Jr., Helotes, TX (US); Jeanie Graciela Lopez, San Antonio, TX (US); Janelle Denice Dziuk, Falls City, TX (US); Paula Ann Whittington, Helotes, TX (US); Donald Nathaniel Holloway, III, San Antonio, TX (US); Jennifer Hunt Erickson, San Antonio, TX (US); Will Kerns Maney, Jr., San Antonio, TX (US); Bradly Jay Billman, Celina, TX (US); Noe Alberto Martinez, San Antonio, TX (US); Jose L. Romero, Jr., San Antonio, TX (US); Bharat Prasad, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 17/385,650

(22) Filed: Jul. 26, 2021

Related U.S. Application Data

(60) Provisional application No. 63/057,716, filed on Jul. 28, 2020.

(51) Int. Cl.
| | | |
|---|---|---|
| A61L 2/24 | (2006.01) | |
| G06F 3/042 | (2006.01) | |
| G06F 3/044 | (2006.01) | |
| A61L 2/10 | (2006.01) | |
| A61L 2/22 | (2006.01) | |
| G01P 13/00 | (2006.01) | |
| G06F 3/01 | (2006.01) | |

(52) U.S. Cl.
CPC ........ *A61L 2/24* (2013.01); *A61L 2/10* (2013.01); *A61L 2/22* (2013.01); *G01P 13/00* (2013.01); *G06F 3/011* (2013.01); *G06F 3/044* (2013.01); *G06F 3/0421* (2013.01); *A61L 2202/14* (2013.01)

(58) Field of Classification Search
None
See application file for complete search history.

(56) References Cited

U.S. PATENT DOCUMENTS

| | | | | |
|---|---|---|---|---|
| 2015/0273786 | A1* | 10/2015 | Ozeki | .............. B32B 27/36 428/41.7 |
| 2018/0027809 | A1* | 2/2018 | Chiattello | .............. A01N 37/18 |
| 2018/0314298 | A1* | 11/2018 | Scaggs | ................. G06F 1/1637 |

* cited by examiner

*Primary Examiner* — Stephen T. Reed
(74) *Attorney, Agent, or Firm* — Plumsea Law Group, LLC

(57) ABSTRACT

A sanitary method and system of providing touch interface experiences to users of public devices are disclosed. In one aspect, the system and method are configured to deploy a clean, protective barrier across a touchscreen for each user of the public device. The barrier includes a transparent membrane that permits the user to provide touch-based inputs to the touchscreen through the barrier. In cases where the touch interface is generated by a projector, the system and method are configured to deploy a membrane that serves as a disposable screen for the projected interface. Once each user completes their session, the system automatically replaces the used membrane with a fresh membrane, ensuring subsequent users are not exposed to contaminants or residue from previous user sessions.

20 Claims, 13 Drawing Sheets

SYSTEMS AND METHODS FOR PROVIDING SANITARY TOUCH INTERFACE EXPERIENCES

CROSS-REFERENCE TO RELATED APPLICATION

This application claims the benefit of U.S. Provisional Patent Application Ser. No. 63/057,716 filed on Jul. 28, 2020 and titled "Systems and Methods for Providing Sanitary Touch Interface Experiences", the disclosure of which is incorporated by reference in its entirety.

TECHNICAL FIELD

The present disclosure generally relates to sanitary mechanisms for interacting with touchscreen panels and other types of touch interfaces, and specifically to a method and system for providing sanitary interfaces to persons accessing services through public devices that rely on touch or other contact-based inputs.

BACKGROUND

Touchscreen panel devices have become a common means for interacting with and providing information. Typically, a touchscreen panel device includes a touchscreen panel sensor, a control circuit for detecting a contact position of an object on the touchscreen panel sensor, electrical interconnects, and a flexible printed circuit (FPC) board. Such touchscreens are integrated with display devices such as a liquid-crystal display or a plasma display, and/or serve as an input mechanism for various types of publicly accessible hardware, for example, ticket-vending machines, automatic teller machines (ATMs), cell phones, tablets, information and service kiosks, game consoles, etc. Thus, the touchscreen panel includes an active area that is transparent as well as sensors that can detect the contact position (approach position). Touch-based interfaces can also be projected onto common surfaces, such as walls, tables, or screens.

Unfortunately, some or all of a touchscreen panel or other common display surfaces can become contaminated by germs during user hand contacts with the display, particularly touchscreen panels that are provided for daily use by a wide range of people (public devices). For example, bacteria and other contaminants can be transmitted from the external display to a person's hands. Bacteria and viruses on the hands may then readily spread the to the person's mouth, to other surfaces, to food, and to other people. The spread of bacteria increases the risk of food poisoning and transmission of diseases. It can be appreciated that many persons are averse to contact with such surfaces. In some cases, device users may try to wrap paper around their hand before touching the control panel in create an antibacterial barrier between the surface and their hand. The paper barrier is ineffective, since bacteria can easily travel through paper. In other cases, users may try to use a piece of clothing such as a part of a shirt sleeve as a barrier between the surface and the hand. While the shirt sleeve may act as a barrier, bacteria can then attach to the user's shirt sleeve, resulting in similar health concerns. Rubber gloves may be effective in using the device sanitarily, though it remains inconvenient to carry, use, and dispose of rubber gloves.

There is a need in the art for a system and method that addresses the shortcomings discussed above.

SUMMARY

In one aspect, a method of providing users of a touchscreen display for a computing device with a sanitary interaction experience. The method includes a first step of automatically dispensing a first film segment across the touchscreen display at a first time, such that the first film segment extends fully over and covers the touchscreen display, and a second step of receiving, after the first time and via a first sensor associated with the computing device, a first set of data. In addition, the method includes a third step of determining, based on at least the first set of data, that a first interaction session between a first user and the computing device has ended. Finally, the method includes a fourth step of automatically replacing, at a second time, the first film segment with a second film segment in response to determining the first interaction session has ended.

In another aspect, an alternate method of providing users of a touch interface projection for a computing device with a sanitary interaction experience is disclosed. The method includes a first step of automatically dispensing at a first time, in range of a touch interface projector, a first film segment, where the first film segment has a surface area sufficient to serve as a projection surface for the touch interface projection emitted by the touch interface projector. The method also includes a second step of receiving, after the first time and via a first sensor associated with the computing device, a first set of data, and a third step of determining, based on at least the first set of data, that a first interaction session between a first user and the computing device has ended. Furthermore, the method includes a fourth step of automatically replacing the first film segment with a second film segment in response to determining the first interaction session has ended by retracting the first film segment and dispensing a second film segment.

In another aspect, a system for providing users of a touch interface with a sanitary interaction experience includes a processor and machine-readable media including instructions which, when executed by the processor, cause the processor to cause a first film segment to be dispensed across a touchscreen display at a first time, such that the first film segment extends fully over and covers the touchscreen display. The instructions further cause the processor to receive, after the first time and via a first sensor associated with a computing device connected to the touchscreen, a first set of data, and then to determine, based on at least the first set of data, that a first interaction session between a first user and the computing device has ended. In addition, the instructions cause the processor to cause, at a second time and in response to determining the first interaction session has ended, the first film segment to be replaced with a second film segment.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1A:
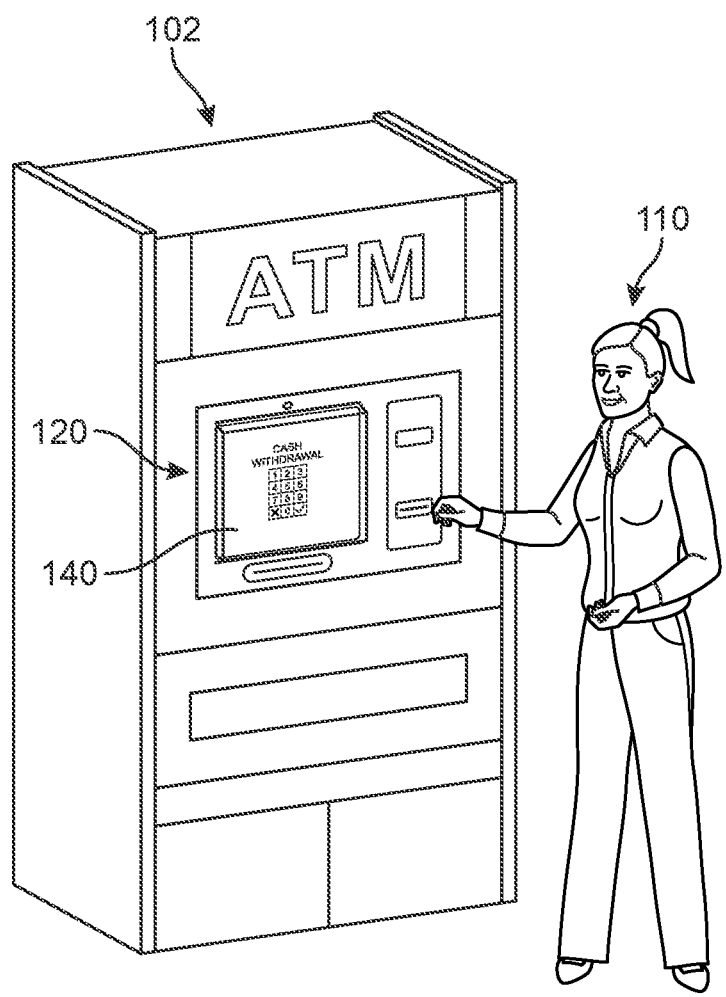
FIGS. 1A and 1B depict a scenario in which a person engages with a touchscreen system that employs a sanitary touch interface mechanism, according to an embodiment.

The embodiments provide methods and systems for allowing users to interact with touchscreen-based devices in a sanitary manner. As described in greater detail below, a clear membrane or other film material can be extended across a surface of a touchscreen panel. The membrane serves as a barrier between the touchscreen and direct contact by users. After each use session, the contaminated membrane is removed and a new or cleansed portion of the membrane is moved into position over the touchscreen panel. The membrane is either reusable (after cleaning) or disposable. In some other embodiments, a touch-sensitive interface can be projected onto the surface of the membrane that is similarly made available on a per-person basis. Such a mechanism ensures each user of the device is protected from undesirable residues left by direct physical contact with previous users of the interface as well as other forms of germ transmission such as coughing and sneezing near the display.

References to various aspects of touch-based input technology will be discussed throughout the following disclosure. For purposes of this application, the term 'touch interface' refers broadly to any type of touch-sensitive user interface, including but not limited to touchscreens, touch panels installed over a computing device display that detect the resistive and capacitive energy of a finger on the touch panels, or projection-based displays where a computer display may be projected on a target projection surface. A target projection surface can be itself a non-interactive surface such as a screen, a wall, a table, a body part, a ceiling. In contrast to touchscreens, which are designed to detect touches made to the surface of the screen, the target projection surface is typically not capable of detecting resistive and capacitive touches, but instead detects interference events between the projector and the target projection surface.

As a general matter, a touch input (i.e., contact with the surface), is a gesture typically performed to interact with the displayed information, and may include a single tap, double tap, swipe, zoom motion, and the like. In some embodiments, a zoom motion and other types of touches may be performed with one or more fingers, cues, or any other pointing devices capable of providing touches to the screen or other projection surface. Thus, touch interfaces make it possible to select an item shown on the display or projection based on detection of a touch occurring at the portion of the surface corresponding to the location where the selected item is being shown.

Other terms will also be used throughout this disclosure. Generally, the term "near" as used herein means close in distance but not in physical contact, about or less than 1 mm apart. The term "periphery" as used herein means the outermost part or region of a component within a precise boundary. The term "front face", display, or screen for a computing device refers to the exposed surface of the device that is associated with the touch interface. For example, a touchscreen is generally comprised of a glass sheet that includes the exposed surface for the operable touchscreen portion. Similarly, the side of the target projection surface upon which a projection is displayed corresponds to the front face or display of that device.

For purposes of clarity, an overview of one embodiment of the proposed systems and methods is illustrated with reference to FIGS. 1A and 1B. In FIG. 1A, an embodiment of a customer 110 engaging with a banking kiosk 102 is presented. In different embodiments, kiosk 102 may comprise an enclosure 100 along with various components and resources that provide banking services for users. In some cases, kiosk 102 could be a stand-alone structure. In other cases, kiosk 102 could be part of a larger building or other structure. The enclosure may provide systems to facilitate banking transactions. As seen in FIG. 1A, an exterior of the enclosure may include an automated teller machine (ATM) 120. Some embodiments of the ATM 120 may include components to provide videotelephony. In other cases, the ATM 120 may be comprised of standard interactive features for viewing and accessing services related to banking.

In different embodiments, the kiosk 102 may communicate with a server via a network. The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP) and file transfer protocol (FTP) as well as other protocols. In some embodiments, the kiosk 102 can be connected to the network through a hardwire connection or wirelessly. Similarly, the server can be connected to a network via a hardwire connection or wirelessly. The server can be used to manage the activity of kiosk 102 and/or to send and receive information to and from kiosk 102. In many cases, the kiosk 102 is designed to be unmanned and/or operated remotely. Thus, kiosk 102 may be potentially operational at any time, and can host interactive sessions 24 hours per day, 7 days a week.

Furthermore, the functionality of ATM 120 is provided by an interactive system that may be accessed by a user via a display panel 140 (or a projected image created by an image projecting device). The ATM 120 may also include one or more slots for scanning, printing, or providing storage for documents, and/or other slots that may provide provisions for the occupant to deposit or withdraw funds in the form of paper money (and/or checks for deposits). In some embodiments, referring to the magnified view of the display panel 140 of kiosk 102 in FIG. 1B, the ATM includes a sensor assembly 160. The sensor assembly 160 could include a camera and a microphone, for example. A camera may capture still or video images of a user that can be transmitted to a server or other party outside of kiosk 102. Likewise, microphones can capture audio that can be transmitted to a party, such as an employee of a bank, outside of kiosk 102. In some embodiments, the sensor assembly 160 includes a motion sensor that detects movement in the area near the ATM 120.

Figure 1B:
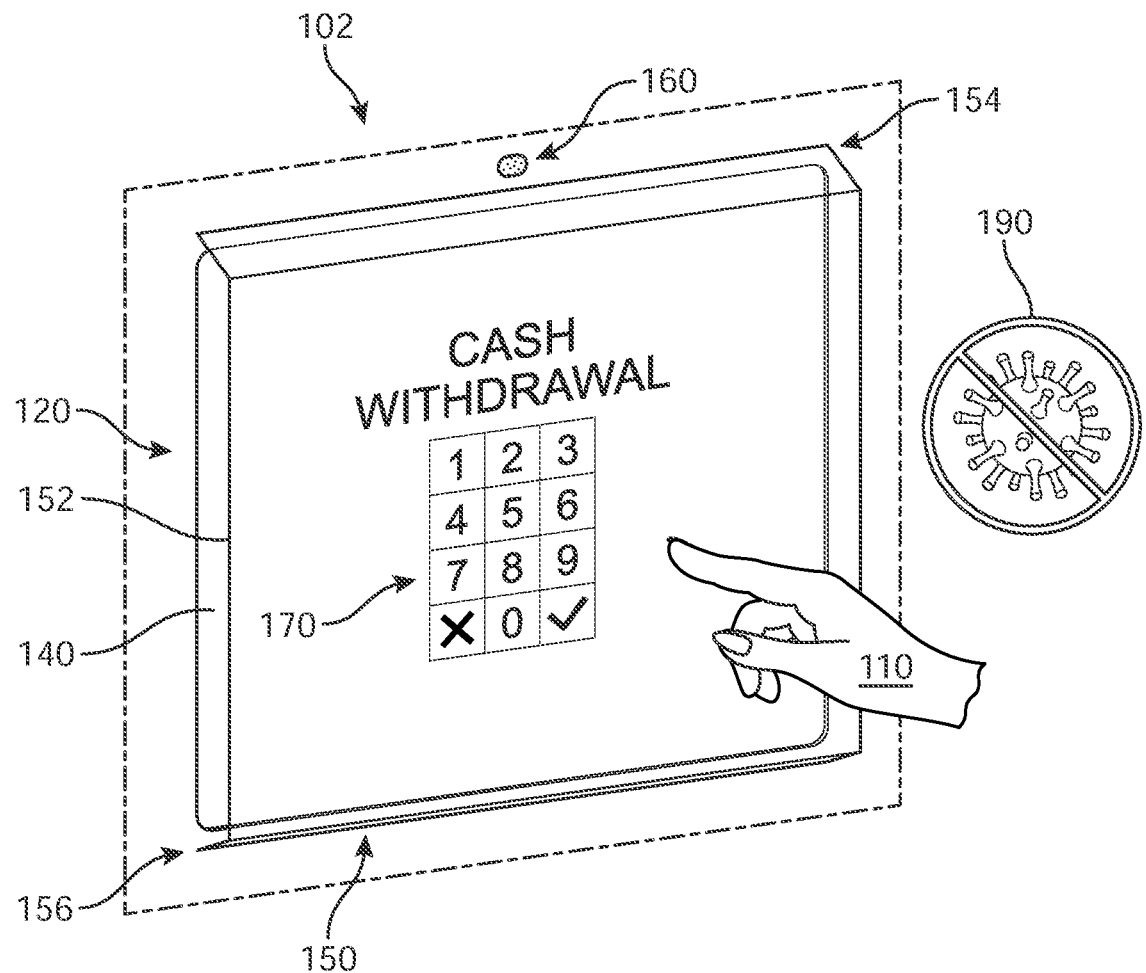

The display panel 140 in FIG. 1B is further associated with a membrane dispenser system 150 that includes a substantially continuous sheet of membrane 152 extending from a first slot 154 to a second slot 156. Before use, the membrane 152 (also referred to herein as a "film") is shown near (but spaced apart) from the front-facing surface of the display panel 140 below or behind the membrane 152. It should be understood that the spacing shown in FIG. 1B, is for purposes of illustration and may be exaggerated to better present the components' positions relative to one another. Thus, in other embodiments, the spacing may be decreased, such that the membrane 152 is nearly touching the display panel 140. In such cases, during use, the membrane 152 may be pressed or pushed proximally inward, toward the display screen, to make contact with the display screen where the user is seeking to make contact, and then become spaced apart again once the pressure is removed. Furthermore, the membrane dispenser system 150 can include additional components, such as a power supply and control circuitry, that may be located within or around the enclosure.

Figure 7A:
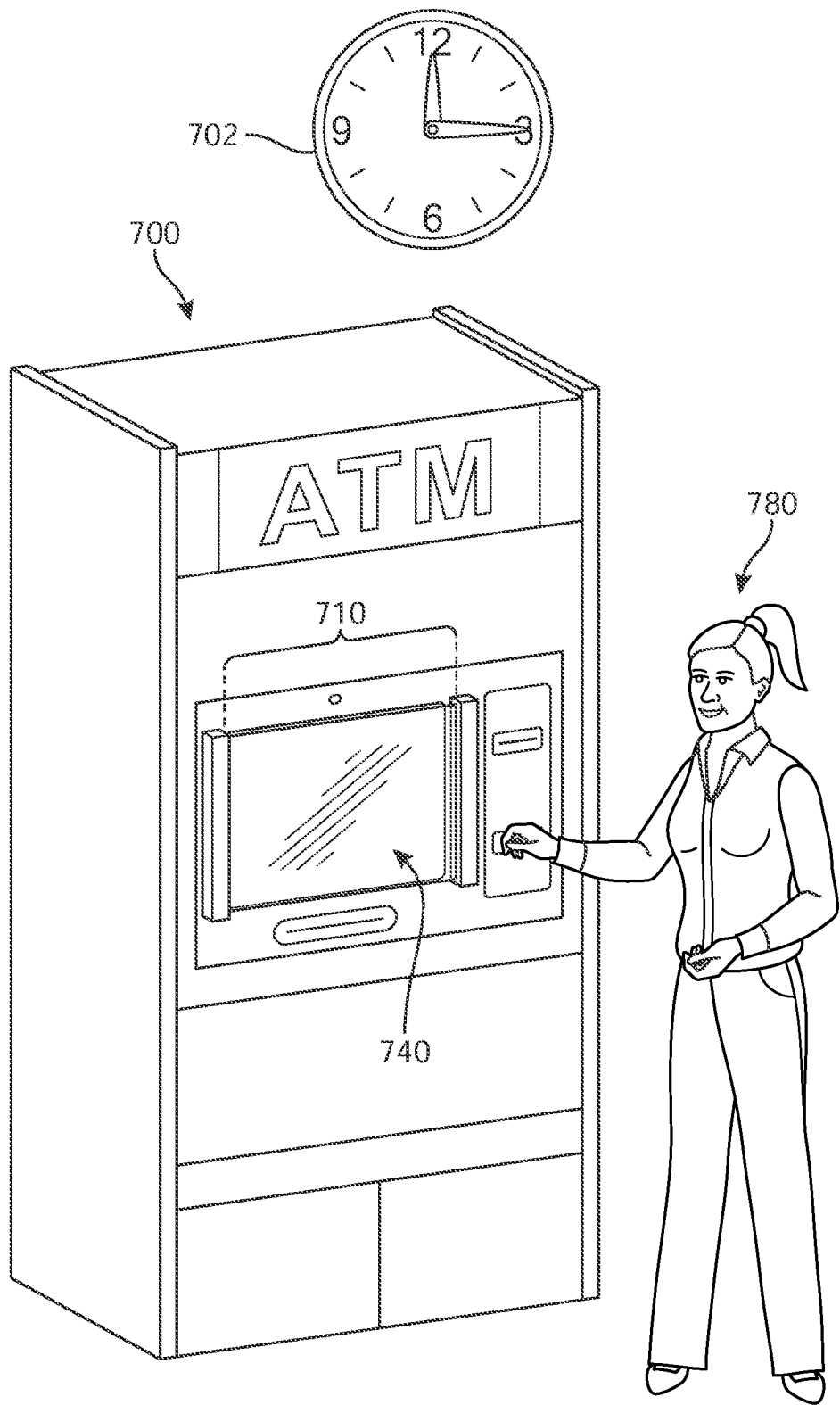
FIGS. 7A-7C are a sequence of drawings depicting a public touchscreen in which a fresh protective film is provided to each new user, according to an embodiment.
Figure 7B:
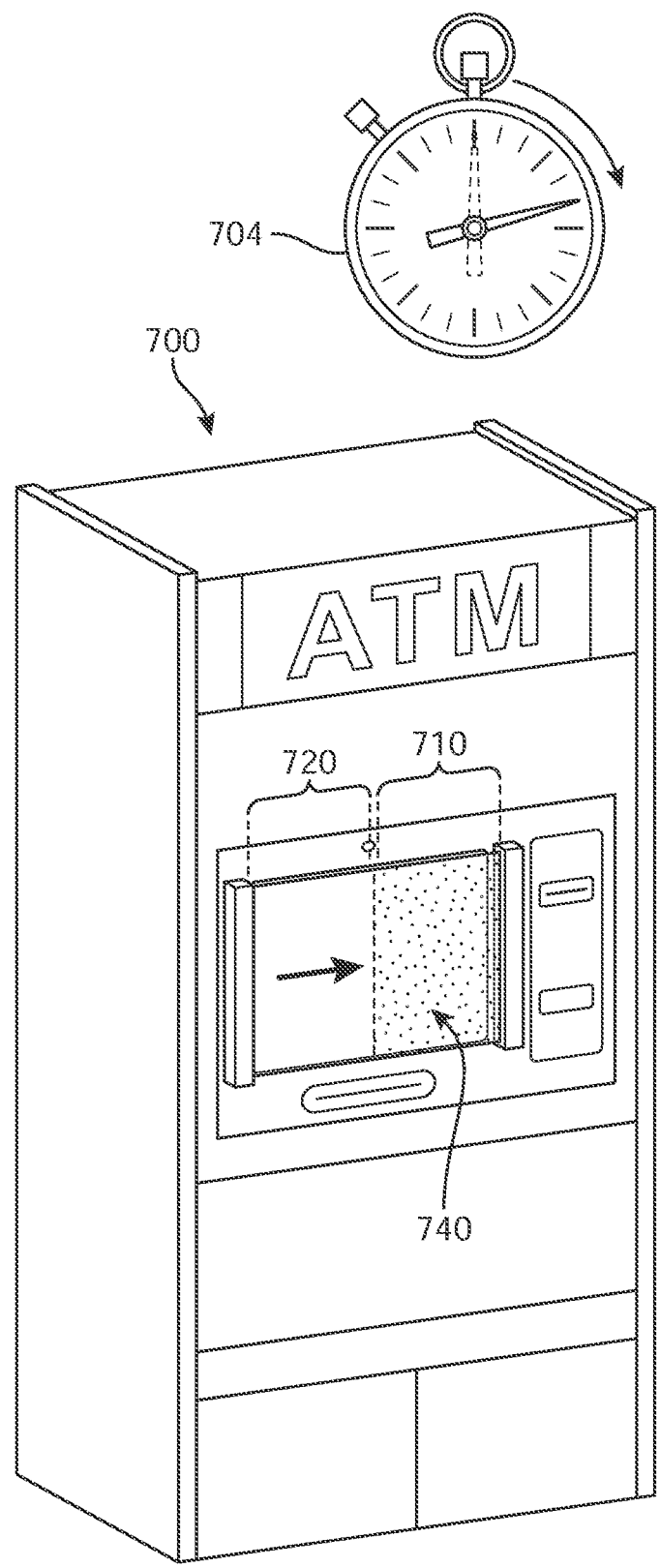
Figure 7C:
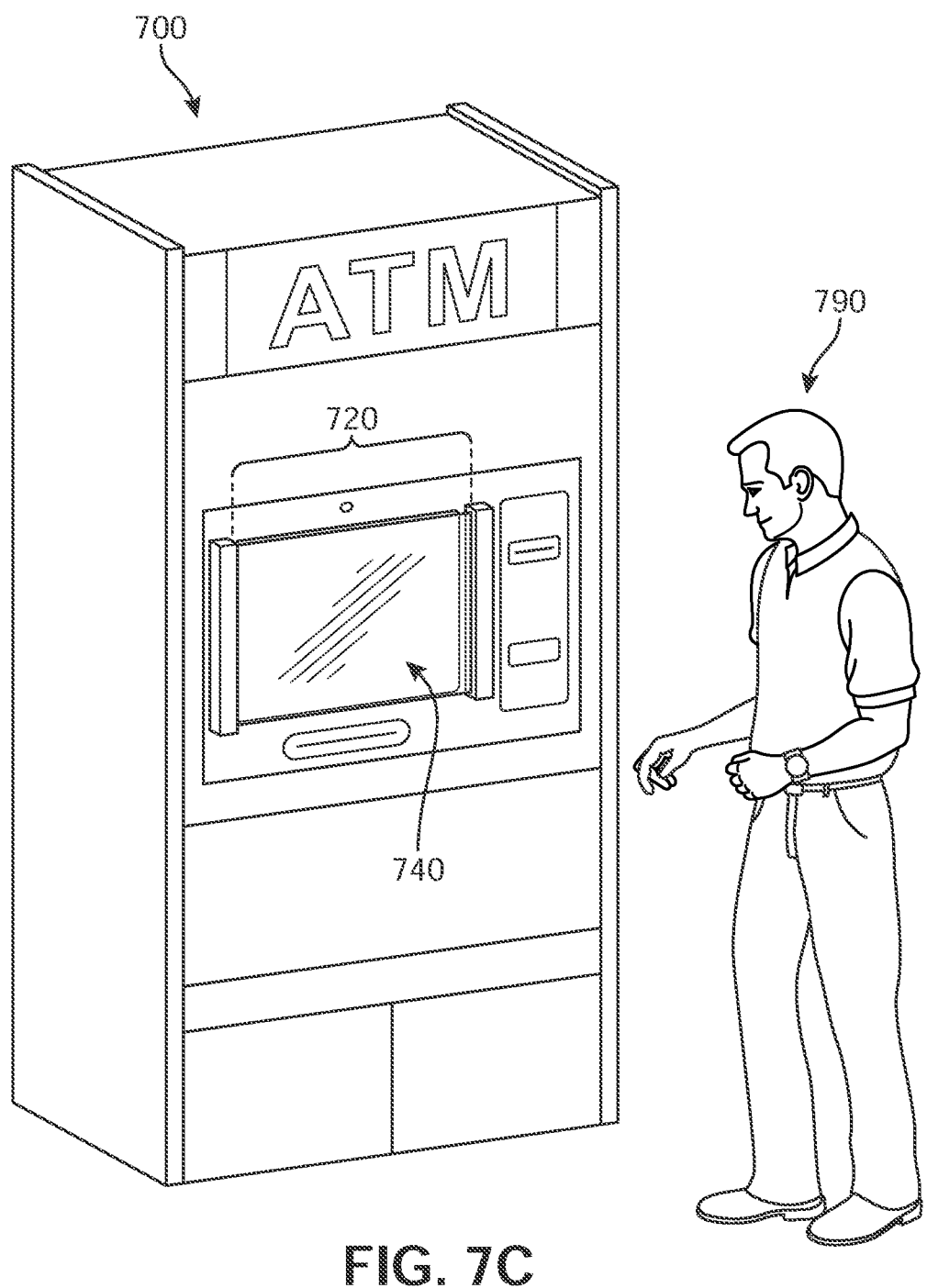

In different embodiments, the membrane can be dispensed before a customer's arrival, or upon detection of the customer's arrival. In FIG. 1A, when the customer 110 walks or moves near the kiosk 102 and/or places a hand or object slightly toward the sensor assembly 160, the sensor assembly 160 is triggered and a signal is then sent thorough an amplifier and processor and to the respective circuitry within a micro controller actuates a dispensing motor in response to the signal. Alternatively, in other embodiments, the dispensing motor is actuated when the system detects that the customer has disengaged with or terminated their use session with the kiosk 102, as illustrated in FIGS. 7A-7C below.

In some embodiments, the dispensing motor can cause a preprogrammed length of membrane 152 to be dispensed via a supply roller that is linked to the dispensing motor. In one example, the motor rotates a second roller that pulls the sheet of continuous membrane wrapped around a first roller. Thus, the second roller serves to receive the used membrane as it is dispensed from the first roller. In some embodiments, the 'used' or previously dispensed membrane 152 will now be removed via one of the slots, while a fresh, cleansed, or otherwise different portion of membrane 152 will be dispensed via the opposite slot. In this example, the membrane 152 emerges from the first slot 154 and is removed via the second slot 156. However, in other cases, the arrangement may be reversed, such that the second slot 156 is configured to dispense the membrane 152 and the first slot 154 to remove the membrane 152. In other embodiments, the sensor assembly 160 may be alternatively or additionally triggered by detection that the customer 110 has moved away from the kiosk 102, such that the sensor no longer receives a signal from the emitter, for some preselected period of time.

Such a system offers customers reliable protection from a wide range of contaminants 190 by ensuring a clean surface is available for each user. For example, as customer 110 reaches out to 'press' a virtual keypad 170 presented on the display panel 140, the membrane 152 serves as a clean barrier between the glass surface and the customer's finger that conveys the touch input through the membrane 152.

Figure 2:
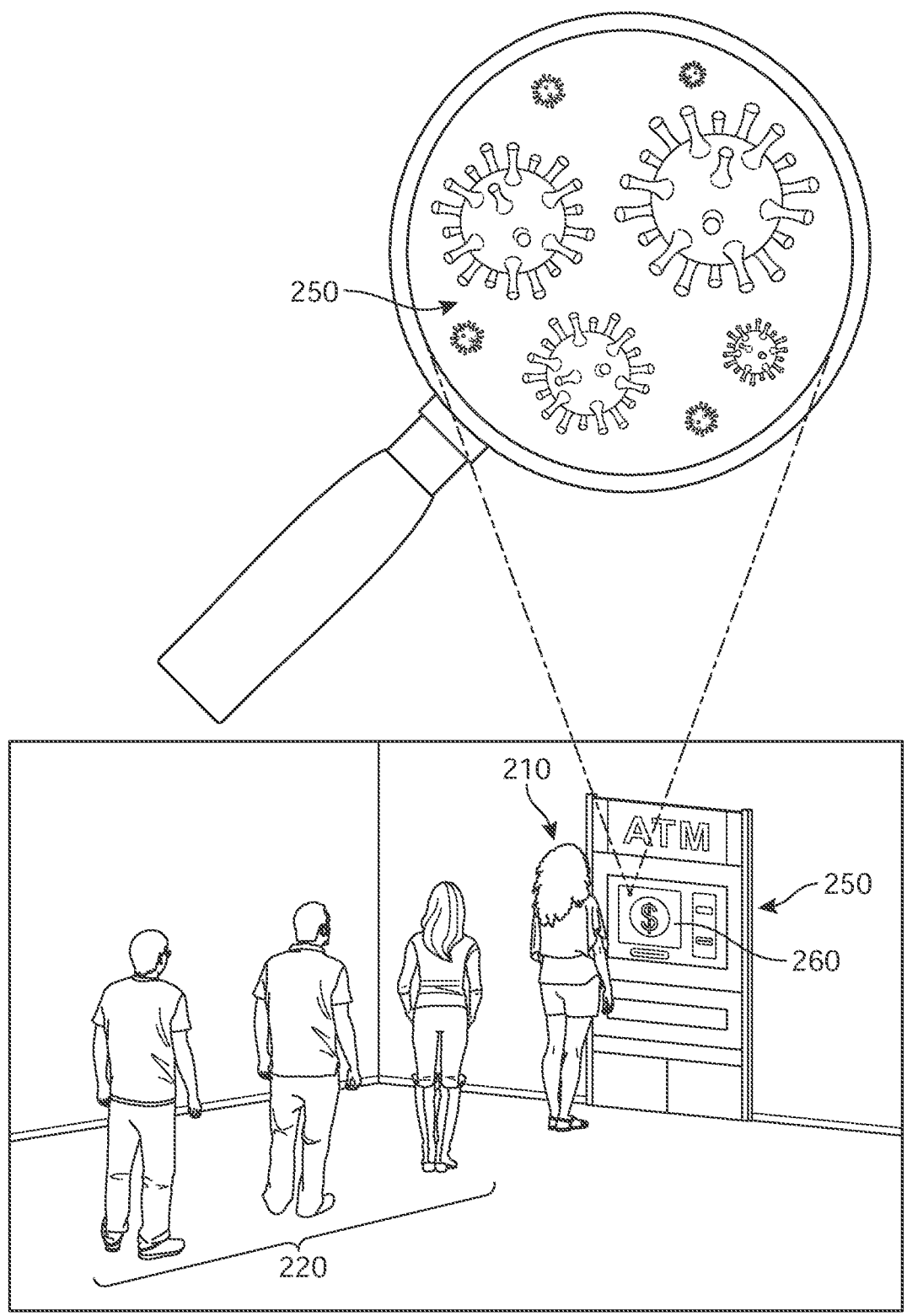
FIG. 2 depicts an example of some drawbacks during use of touchscreens for public computing devices, according to an embodiment.

This type of sanitary interaction is useful across all types of touch interfaces. More specifically, in terms of exposure, machines employing touch interfaces that are designed for use in common spaces or public settings have been identified as transmission exchange stations for a wide range of contaminants. For purposes of context, FIG. 2 depicts a queue 220 for an ATM 250 at which a first user 210 is currently located. As each user moves to the front of the queue 220, additional microorganisms, food particles, body fluids, and germs 270 are conveyed to a screen 260 of the ATM 250. Throughout the course of a single day, the ATM 250 can serve hundreds of customers. Typically, the screen is not disinfected between customers, and there are hundreds of fingers interacting with options presented on a touch-screen, such that the surface becomes rife with bacteria. For example, bacteria that cause food-borne illness—including *Salmonella* and a pathogenic strain of *E. coli*—have been shown to survive for days on ATMs. One test conducted by Kimberly-Clark Corp. as part of its Healthy Workplace Project showed that 41% of automated teller machines carry germs that can cause colds and the flu. Furthermore, ATMs were number four on their list of most-contaminated public surfaces.

In another powerful example, the proposed systems and methods can be implemented in healthcare applications. Electronic devices with touchscreens are increasingly used to access electronic patient records. These devices must be sterilized repeatedly. By offering a convenient membrane barrier the devices can be readily utilized by multiple medical professionals without fear of contamination among staff and patients. Other environments in which touch-screens are relied on and used by multiple persons (i.e., public devices) would also benefit from such arrangements.

Figure 3A:
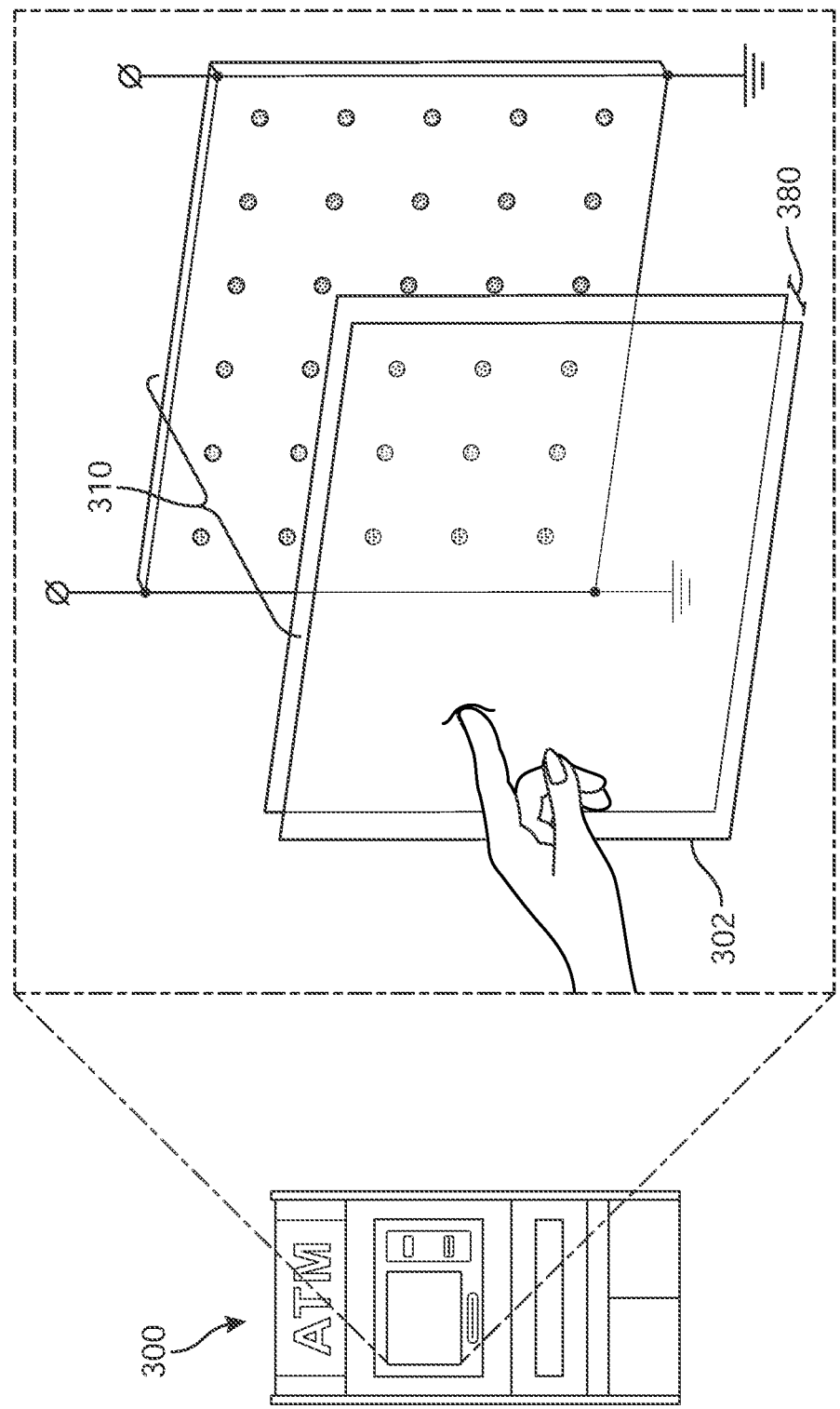
FIGS. 3A and 3B are two views of an example of a protective film being applied over a touchscreen, according to an embodiment.
Figure 3B:
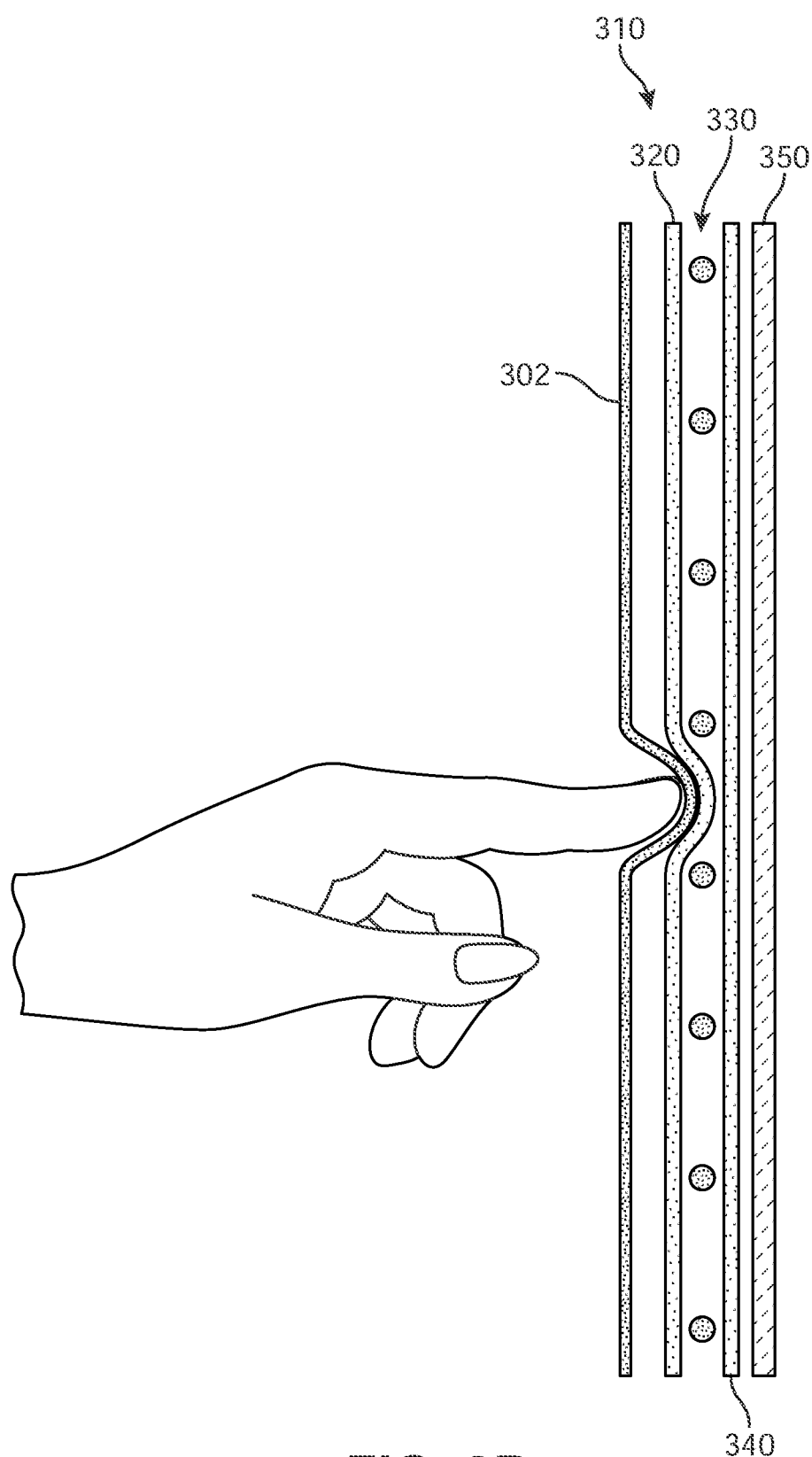

Referring now to FIGS. 3A and 3B, for purposes of clarity, an example of an external film layer ("film") 302 applied to a capacitive (resistive) touch panel system 310 for a computing system 300 employing a touch interface is shown. In FIG. 3A, an isometric front view of the touch panel is shown, and in FIG. 3B, a side view of the touch panel is shown. The touch panel system 310 generally includes a capacitive touch panel such as a glass or other transparent display panel ("panel") 350, coated or covered with a transparent conductive screen 390. When any part of a human body (an electrical conductor) touches the surface of the screen 390 results in a distortion of the panel's electrostatic field, measurable as a change in capacitance. In different embodiments, the panel 350 may be combined with a display, such as a liquid crystal display (LCD) or projected capacitive (PROCAP) touch panel, which may optionally include an LCD or other display, allowing finger or other touches to be sensed through the film 302 disposed in front of the conductive screen 390 of the panel 350.

In this example, the screen 390 is composed of two conductive, relatively transparent layers (e.g., indium-tin-oxide (ITO)), which are held separated at a small distance by spacer dots 330. Along a bottom conductive layer 340, a small voltage is alternatingly applied in x- and y-direction, while a top conductive layer 320 connects to the second half of the circuit. Typically, these are capped by a stiff but bendable layer and directly sit on the actual display. Applying pressure to the screen bends the conductive layer on top and closes the circuit. The resulting currents along the x- and y-circuits can be measured and provide information about where the circuits are closed. In addition, a processor detects the touch position on the touch panel.

In other embodiments (not shown here), the touch interface can be part of a system employing projected capacitive screens, in which the screens are composed of two grids, rotated at 90° to each other, of very fine conductive wires with spacers in between. In contrast to the resistive screens, they do not form a continuous layer; rather, the ITO grids create large numbers of crossings, which act like small capacitors whose capacity changes whenever a conductive or dielectric object (like a finger) approaches the grid. A digital controller measures the capacity of all grid points one by one and if a certain deviation from the saved standard value is reached, a touch is registered. This technology allows multi-touch applications since all grid-points are measured separately and the image quality is enhanced due to the lower amount of ITO between the user's eye and the actual display. Other touchscreen technologies may also be used in conjunction with the proposed membrane film layer, such as those based on infrared light, inductive coils, sound, the piezoelectric effect, etc.

In different embodiments, the film 302 can cover or extend across some or all of the surface of the touch-sensitive screen 390. The film 302 can be made of any suitable material that permits the user to interact with the display screen of the electronic device through the film 302 (i.e., is conductive) and/or otherwise allows for the transmission of electrical energy from a human hand to the touch-sensitive screen. In some embodiments, film 302 can comprise a flexible, plastic layer such as a thin layer of polycarbonate (e.g., LEXAN®), polyvinylchloride, high-strength alkali-aluminosilicate thin sheet glass (e.g., GORILLA GLASS®), urethane, silicon, polyethylene terephthalate (PET), or any other suitable material. The film 302 can be formed using any suitable manufacturing process, such as thermoforming, casting, stretching, heating, or injection molding. In some cases, film 302 includes a thin, transparent, flexible layer of polyurethane. In addition, film 302 can have any suitable thickness, including but not limited to a thickness of about 0.0001-0.001, 0.0001-0.01, 0.001-0.100, 0.001-0.050, 0.004-0.020, 0.005-0.015, or 0.005-0.010 inches. While the embodiments include the use of transparent membranes with touchscreens, it can be appreciated that either transparent and non-transparent membranes may also be used in embodiments in which the touch interface is provided by a projector device (see FIG. 6).

In some embodiments, film 302 can include one or more openings that facilitate access to or the use of one or more features of the computing device 300, such as a microphone, speaker, camera, or button. In one embodiment, film 302 includes an anti-reflective (AR) coating, such as an optical coating applied to the surface of film 302 to reduce reflection. In one example, the AR coating can include a transparent thin film having a plurality of alternating layers with contrasting refractive indexes. The AR coating can be selected to perform across a wide range of wavelength ranges, including infrared, visible, and ultraviolet ranges. In another example, film 302 may include a privacy filter that permits viewing of the touchscreen display by a user who is directly in front of the display, but restricts viewing of the display by another person who is not directly in front of the display, such as a person standing beside the user, thereby helping prevent confidential information from being viewed by the other person. In some embodiments, the film 302 includes a scratch-resistant coating and/or antimicrobial coating.

Furthermore, as noted earlier, the distance between the film 302 and touch panel system 310 can vary, although preferably the spacing will be minimal. In one example, such a distance 380 is between approximately 0.05 and approximately 1 mm. In one embodiment, the distance can be arranged to be as small as possible while ensuring the film 302 is not in contact with the touchscreen (when the computing device is not being used). Though a stiffer film is desirable in maintaining the distance 380 and supporting the weight of the film, the hardness of the film should also be selected to be flexible enough to accommodate the user's ability to operate the touchscreen. For example, in some embodiments, the hardness of the film can be greater than 1H-2H (i.e., referring to Pencil Hardness Test), while remaining sufficiently thin such that its elasticity permits normal interaction by a user of the touch interface, and a user's finger may be used to press any point of the film against the touchscreen portion of device. By maintaining a distance between the film 302 and the outer surface of the panel system 310 when not in use, a clear, smooth, flat surface is provided without irregularities, bumps, or other non-uniformities on the rear surface of the film that would otherwise press against the display panel and potentially distort the view of the screen for a user. Likewise, distance 380 facilitates the easy removal of the film 302 after use, while minimizing residue on the touchscreen itself.

In different embodiments, the proposed system includes provisions for automatically dispensing the film across the touchscreen and removing and replacing the film after use. As one non-limiting example, in FIG. 4A, two rollers are depicted, including a first (dispensing) roller 410 and a second (receiving) roller 420 that are spaced apart from one another. A first film segment 402 extends between the two rollers. In one embodiment, a motor (not shown) is connected to the second roller 420 and, when activated, rotates the second roller 420 to pull or "take up" the first film segment 402 onto the second (retracting) roller 420 while a new, second film segment is unrolled or unwrapped from around the rotating first roller 410. Thus, in this case, the first roller 410 is a supply roller which includes a substantially continuous sheet of film. At rest, the film is stretched tight over and across the entire surface area of the touchscreen panel.

Figure 4A:
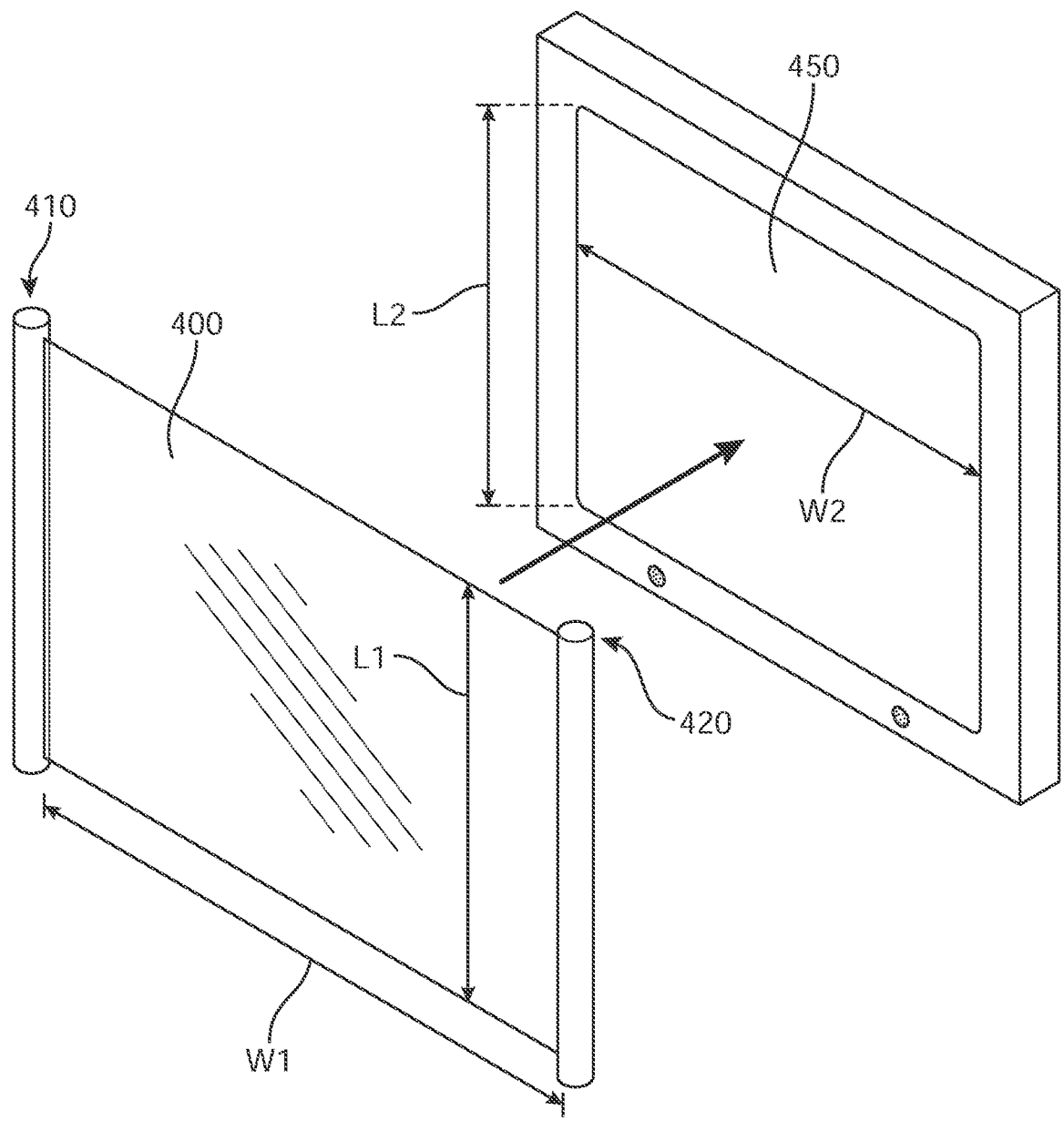
FIGS. 4A and 4B illustrate an example of an external roller system for dispensing a protective membrane over a touchscreen, according to an embodiment.
Figure 4B:
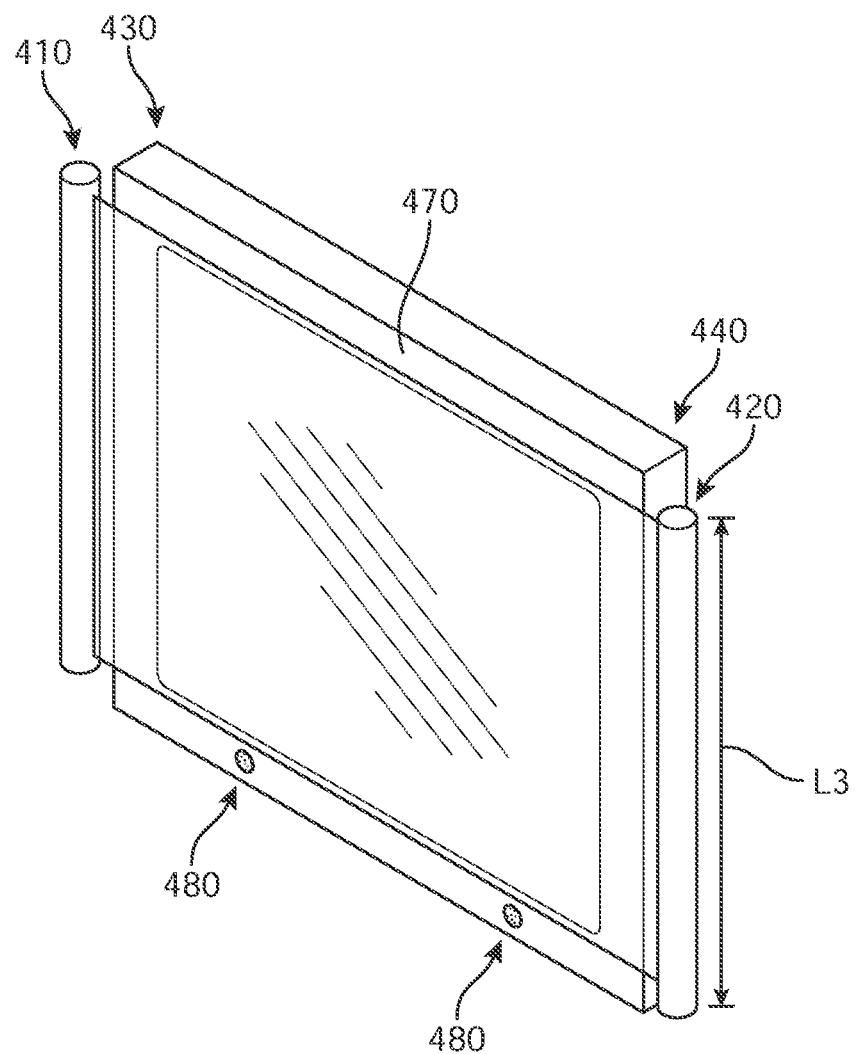

In addition, in some embodiments, one or both of the rollers can be spaced apart by a first width (W1) that is substantially similar to or slightly greater than a second width (W2) of corresponding touchscreen 450, where first width (W1) also refers to the width of the first film segment 402 as it extends across the screen. Similarly, a first length (L1) of the first film segment 402 is substantially similar to or slightly greater than a second length (L2) of the corresponding touchscreen 450. These dimensions ensure that the exposed film segment fully covers the screen, as shown in FIG. 4B. Each roller is secured or installed along two opposing sides of the touchscreen 450. For example, first roller 410 is disposed along an outer periphery of a first side 430 of an external enclosure 470 of the touchscreen 450, and second roller 420 is disposed along a second side 440 of the enclosure 470. In cases where the film extends vertically across the touchscreen (e.g., see FIGS. 1A and 1B), the rollers are instead secured directly above and below the touchscreen and have a length equal to or greater than the width of the touchscreen.

By securing each roller along the outer peripheral edge of the enclosure 460, the distance between the film and the touchscreen can be minimized, and coverage across the entirety of the screen is ensured. In some embodiments, for example, adjacent to or along the bottom front periphery of the enclosure 470 are infrared sensors 480 configured to sense the presence (and/or absence) of an object such as a person (used to trigger the motor connected to roller(s)) for a preselected period of time. In other embodiments, the computing system for which the touch interface is being employed can receive data that allows the system to determine when a user interaction session with the system has begun and ended, including but not limited to insertion and removal of a credit/debit card or other identification card, a biometric signal, voice activation, authentication and de-authentication actions, closing of a service or application offered by the computing device, and other log in/log out events. In response to a determination that a user interaction session has ended, the system can send an actuation signal to the motor to initiate a transition to remove the used film and extend a fresh portion of film over the touchscreen or replace the touch screen film deployed for the projector (see FIG. 6).

In some embodiments, when the first roller 410 fully dispenses the available film, the film may be pulled completely off of the first roller 410 and retracted or wound about the second roller 420, exposing the touchscreen beneath, indicating to a potential user that the barrier is no longer available. In other embodiments, an LED may be switched on, or some other message or signal presented to warn of a roller that is nearly depleted or has become depleted for servicing personnel to replace the rollers. In some embodiments, the used film can be sent for cleaning and then reinstalled for use again. In other embodiments, the film supply and retraction rollers may be designed for one-time use and discarded and replaced by new film rollers. In one embodiment, the second roller 420 can include a cleaning function where, before each film segment is returned and wrapped around the second roller 420, the film passes through a purification and/or sanitizing mechanism that allows the film to be recycled and prepped for future use, including, for example, exposure to UV light, disinfectant spraying, and/or wipe and drying mechanisms. The system can then be configured to switch the function of two rollers, such that the second roller 420 becomes the dispensing source and the first roller 410 the receiving or retracting end. In addition, though not shown in FIGS. 4A and 4B, one or both rollers may be individually disposed, held, and/or secured within an external housing with a slot, such as a rigid cylindrical tube or tunnel. The housings can be removably attached to the sides of the enclosure and include a rail or other fastener mechanism for quick removal and reinstallation into the correct position. The placement of the rollers on the exterior of the enclosure allows any personnel to make adjustments and/or replace rollers as needed.

Alternatively, in some embodiments, the rollers may be disposed within or behind a portion of the housing for the touchscreen, rather than be located along the external surface of the touchscreen. For example, in FIG. 5, an ATM 500 is illustrated with a magnified, exploded, phantom (dotted-line) view of a touchscreen display assembly 550 that includes a touchscreen 540 covered by a portion of film 502. In this case a first roller 510 and a second roller 520, operating in a manner similar to the mechanism shown in FIGS. 4A and 4B, are shown disposed behind the touchscreen 540. In other words, the rollers are located internally within an enclosure 590 of the ATM 500, rather than being positioned externally. A forward enclosure section 592 supports the touchscreen assembly 550, here comprising a rigid panel with a window opening for the touchscreen 540 and input mechanisms 560 for card dips and/or insertion or dispensing of cash or checks or other user inputs and system outputs.

The forward enclosure section 592 further includes two parallel elongated apertures or slots, here shown as a first slot 582 and a second slot 584. The two slots are formed along opposite sides of the touchscreen 540 and are substantially equal in length. Furthermore, the length of each slot is equal to or greater than the length of the adjacent touchscreen 540. In cases where the film extends vertically across the touchscreen (e.g., see FIGS. 1A and 1B), the slots are instead formed directly above and below the touchscreen 540 and have a length equal to or greater than the width of the touchscreen, and the internally disposed rollers are also oriented and positioned to correspond to the slot arrangement.

Thus, in this embodiment, the film extends outward from the first roller 510 located within enclosure 590 and is routed or passed through first slot 582 to emerge outside of the enclosure 590. The film 502 then extends across the entire exposed surface area of touchscreen 540, and is routed or passed through the second slot 584, returning to an interior of the enclosure 590 to be wrapped around second roller 520. In this case, because the rollers are maintained within the enclosure 590, the likelihood of tampering or accidental damage is reduced. However, access to replace or modify the film also becomes limited to those with personnel with authorization to remove the forward enclosure section 592.

In some embodiments where the film is sanitized or treated after use, as discussed above, the proposed arrangement can optionally include provisions for automatically returning the cleaned film to the first roller for re-use. Simply for purposes of illustration, in FIG. 5, one example of a return mechanism is shown, where a cleansed portion 504 emerges from second roller 520 and extends across to the first roller 510 in anticipation of the subsequent application across the touchscreen 540, providing a substantially continuous loop that can be used across multiple interaction cycles. As another, alternate example, the first portion of film can be removed and replaced by a second portion of film. The first portion of film may then be cleansed by the second roller and the system reversed, such that the second portion of film is removed and replaced by the first portion of film from the second roller, and the second portion of film is cleansed by the first roller. In other words, the same two, three, or four portions of film may be used in a repeating, alternating cycle of use, removal, sanitization, and re-use, depending on the roller and cleaner mechanism arrangement.

Figure 5:
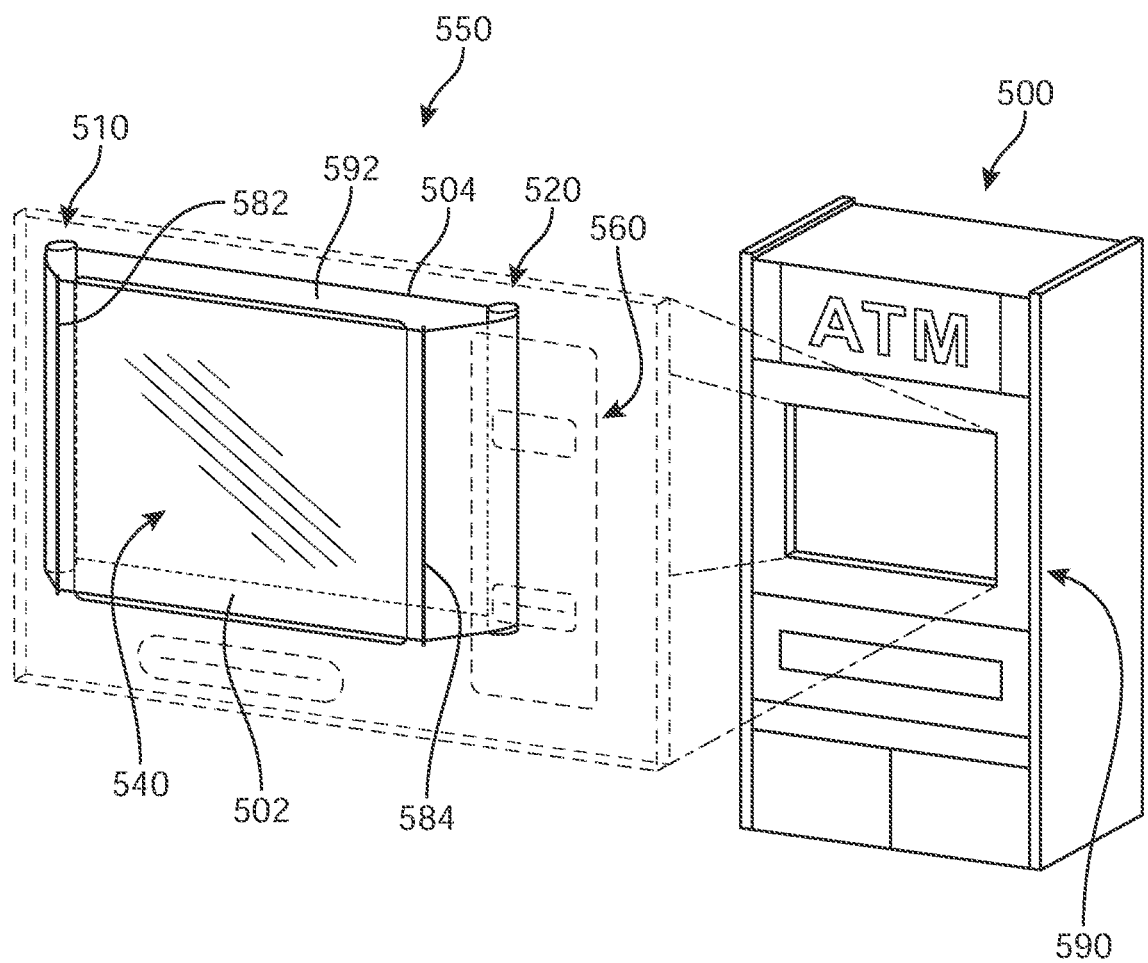
FIG. 5 is an illustration of an example of an internal roller system for dispensing a protective membrane over a touchscreen, according to an embodiment.

It should be appreciated that the film described herein offers the advantage of being able to be installed and/or replaced easily and quickly, without any adverse effect on the appearance and display quality of the touchscreen portion of the underlying computing device. It should be understood that the configurations presented in FIGS. 4A, 4B, and 5 are for purposes of illustration only, and other embodiments may utilize different or additional components, mechanisms, and processes, or omit one or more components shown.

Figure 6:
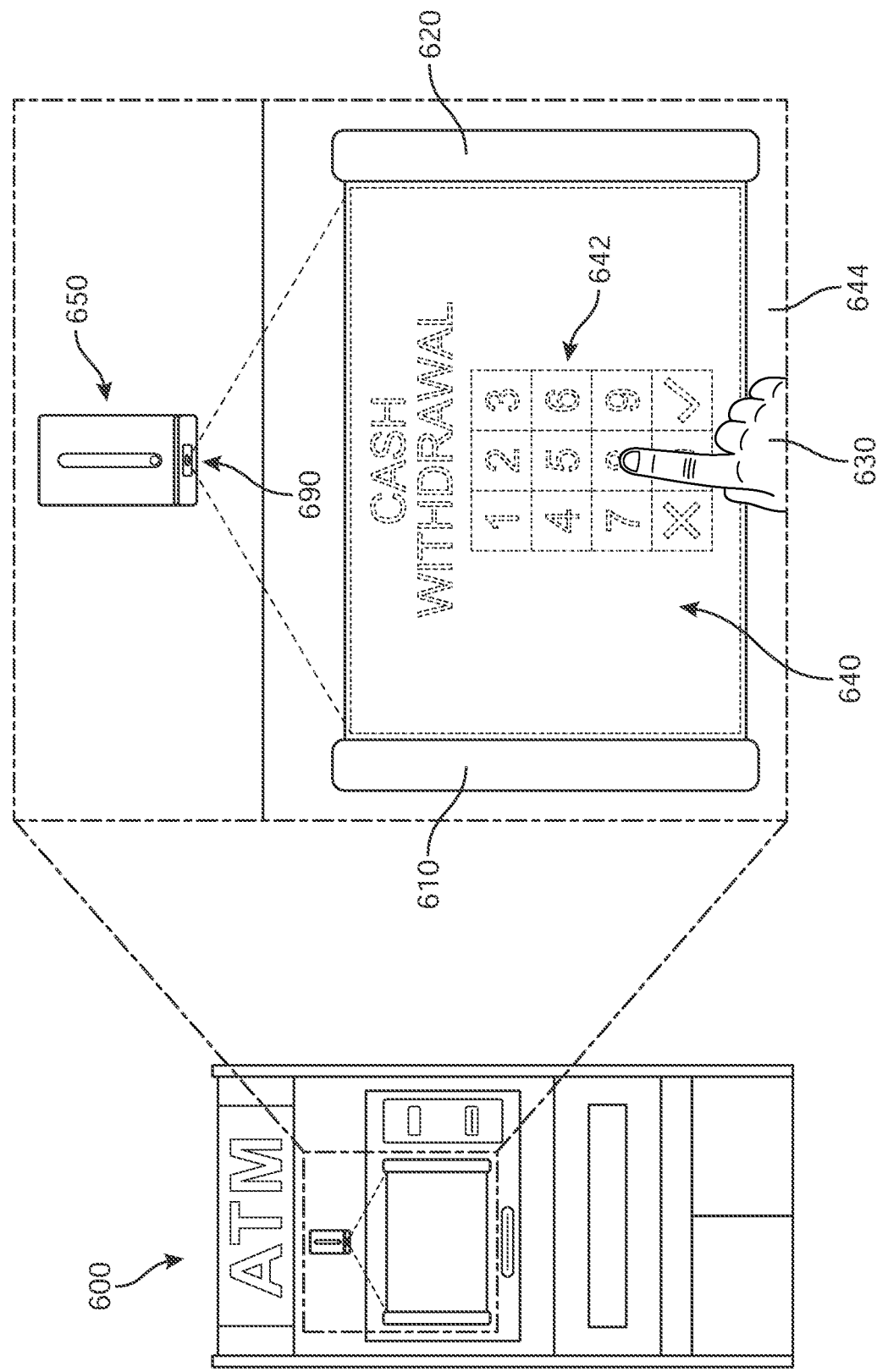
FIG. 6 is a top-down view of a protective membrane being used as a screen for a projector-based touch interface, according to an embodiment.

As noted earlier, touch interfaces can also be provided by use of a projection system. FIG. 6 is an example of a public computing device 600 in which a touch interface 642 is projected via a projection device ("projector") 650 onto a screen surface comprising a membrane-based projection sheet ("projection sheet") 640. In different embodiments, a projector may include any projector or micro-electrical-mechanical system (MEMS) that can project optical radiation in two forms: visible optical radiation providing the colored light of each frame and invisible optical radiation which is used to determine the depth of the pixels in each frame. The projector is then able to determine information about the depth of each of the projected pixels, and provide this depth information to a connected computing device. The computing device can then determine the actual depth of each projected pixel, where the target projection surface is, and where one or more pointer(s) may be located. With this information, it is possible to determine whether a touch is occurring. For purposes of this application, the term "in range of" a touch interface projector refers to an object or surface that is near enough to the projector to serve as a functional target surface for the optical radiation emitted by the projector.

The projection sheet 640 may be any generally planar or even non-planar material that may reflect the projected frame and/or serve as a screen. The projection sheet can be supported or extend between two rollers (e.g., a first roller 610 and a second roller 620), and may further be disposed across a base surface 644 such as a wall, ceiling, floor, textured surfaces of varying sizes and shapes, panel, or other surfaces. The surface area of the projection sheet 640 may vary in size depending on the requirements of the computing device 600 and services being provided. However, the surface area should at a minimum be of a size sufficient to receive and display the projected image(s) transmitted by the projection system. A user 630 (represented by a hand) is shown making contact with the projection sheet 640 in order to select options presented by the projected touch interface 642. In some embodiments, when a touch is occurs at the projection sheet 640, sensors 690 for the projector 650 can detect the change to the projection surface, or where a projected pixel actually lands. In this example, after the user 630 concludes their interaction session with the touch interface 642, the rollers can be triggered via a mechanism similar to those discussed with reference to FIGS. 4A-5 to remove the used portion of the projection sheet and dispense a fresh portion of the projection sheet.

In different embodiments, the projection sheet 640 can comprise the membrane material as described above. However, in cases in which a projector device is used (rather than a touchscreen display panel) the projection sheet 640 can include a wide variety of materials that can be transparent, translucent, or opaque, and can vary in terms of thickness from the membrane described earlier, as there is no display screen beneath the projection sheet 640 that must remain visible and/or protected. In some embodiments, the projection sheet 640 can include paper, plastic, or even fabric or cloth, or any material that can be readily and repeatedly dispensed and removed.

For purposes of clarity, FIGS. 7A-7C present a sequence in which a public device 700 implementing a sanitary touch mechanism is accessed by a first customer 780 and a subsequent, second customer 790. When the first customer 780 approaches the public device 700 in FIG. 7A, a first film layer ("first film") 710 is present and extends above or in front of a touchscreen panel 740. The first customer 780 interacts with the touchscreen panel 740 over a first time period 702, during which the first film 710 remains in place and serves as the receiving surface for the touch-based inputs provided by the first customer's fingers, sharing or conveying these inputs to the touchscreen panel 740 below. In FIG. 7B, sensors for the public device 700 register the departure of the first customer 710 and the absence of any movement for a minimum period of time. In response, the system is configured to cause the sanitary touch mechanism to be triggered and remove the first film 710, as well as dispense a second film layer ("second film") 720. As shown in FIG. 7B, over a second period of time 704, the transition between the used segment of film and the fresh segment of film is depicted. The second period of time 704 can vary based on the size of the film being dispensed and the power of the motor. The transition cycle is completed when the second film 720 extends fully across the touchscreen panel 740 and the first film has been fully removed, as shown in FIG. 7C, and a second customer 790 approaches ready to interact with the sanitized surface again provided by the system.

Figure 8:
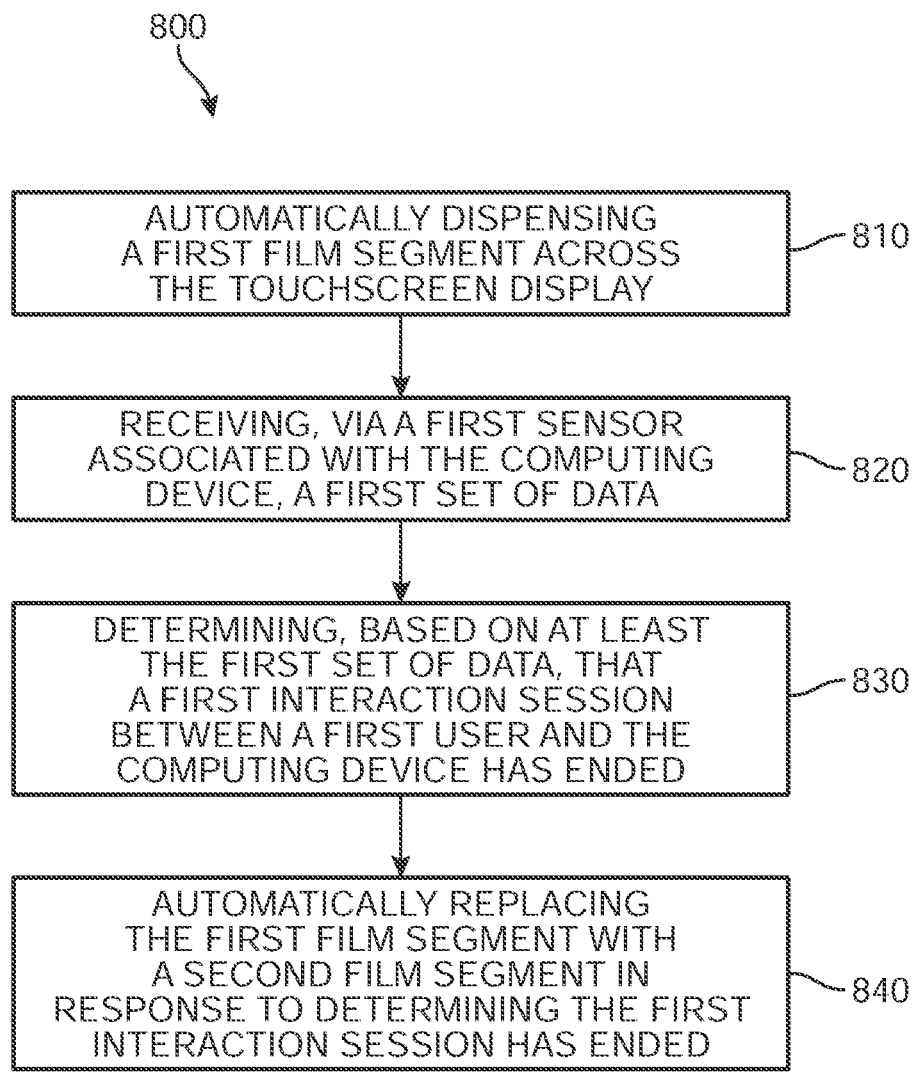
FIG. 8 is a flow chart depicting a process for providing users of a touchscreen display for a computing device with a sanitary interaction experience, according to an embodiment.

FIG. 8 is a flow chart illustrating an embodiment of a method 800 of providing users of a touchscreen display for a computing device with a sanitary interaction experience. The method 800 includes a first step 810 of automatically dispensing a first film segment across the touchscreen display at a first time, such that the first film segment extends fully over and covers the touchscreen display, and a second step 820 of receiving, after the first time and via a first sensor associated with the computing device, a first set of data. The method also includes a third step 830 of determining, based on at least the first set of data, that a first interaction session between a first user and the computing device has ended. The method further includes a fourth step 840 of automatically replacing, at a second time, the first film segment with a second film segment in response to determining the first interaction session has ended.

In other embodiments, the method may include additional steps or aspects. In some embodiments, the method also includes obtaining the first set of data from a motion sensor located on or near a periphery of the touchscreen display. In another example, the method further includes detecting, at the computing device, a sign-out event by the first user (i.e., such that the user has closed their session or terminated access of the services offered by the computing device), and the first set of data includes the detected sign-out event. In some embodiments, the method can include additional steps of receiving, after the second time and via the first sensor, a second set of data, determining, based on the second set of data, that a second interaction session between a second user and the computing device has ended, and then automatically replacing, at a third time, the second film segment with a third film segment in response to determining the second interaction session has ended. In one embodiment, the dispensed first film segment is spaced apart from the touchscreen display when the touchscreen display is not in use. In another example, the first film segment and the second film segment correspond to two distinct portions of a continuous sheet of film (e.g., wrapped around a roller).

Other methods may be contemplated within the scope of the present disclosure. For example, in some embodiments, a method of providing users of a touch interface projection for a computing device with a sanitary interaction experience includes a first step of automatically dispensing at a first time, in range of a touch interface projector, a first film segment, where the first film segment has a surface area sufficient to serve as a projection surface for the touch interface projection emitted by the touch interface projector. The method further includes a second step of receiving, after the first time and via a first sensor associated with the computing device, a first set of data, and a third step of determining, based on at least the first set of data, that a first interaction session between a first user and the computing device has ended. Furthermore, the method can include a fourth step of automatically replacing the first film segment with a second film segment in response to determining the first interaction session has ended by retracting the first film segment and dispensing a second film segment.

In other embodiments, this method may include additional steps or aspects. In some embodiments, the method also includes obtaining the first set of data from a motion sensor located on or near a periphery of the dispensed first film segment. In another example, the method further includes detecting, at the computing device, a sign-out event by the first user (i.e., such that the user has closed their session or terminated access of the services offered by the computing device), and the first set of data includes the detected sign-out event. In another example, the method includes further steps of receiving, after the second time and via the first sensor, a second set of data, determining, based on the second set of data, that a second interaction session between a second user and the computing device has ended, and then automatically replacing, at a third time, the second film segment with a third film segment in response to determining the second interaction session has ended.

In one embodiment, the first film segment and the second film segment correspond to two distinct portions of a continuous sheet of film (e.g., wrapped around a roller). In another embodiment, the first film segment is opaque (e.g., a solid white or another color light enough to present the projected images), thereby serving as a display surface. In some embodiments, the method also includes sanitizing the first film segment when the first film segment is retracted, and wherein the third film segment includes the sanitized first film segment.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A method of providing users of a touchscreen display for a computing device with a sanitary interaction experience, the method comprising:
    automatically dispensing a first film segment across the touchscreen display at a first time, such that the first film segment extends fully over and covers the touchscreen display;
    receiving, after the first time and via a first sensor associated with the computing device, a first set of data;
    determining, based on at least the first set of data, that a first interaction session between a first user and the computing device has ended; and
    automatically replacing, at a second time, the first film segment with a second film segment in response to determining the first interaction session has ended.

2. The method of claim 1, wherein the first film segment and the second film segment correspond to two portions of a continuous sheet of film.

3. The method of claim 1, further comprising obtaining the first set of data from a motion sensor located on or near a periphery of the touchscreen display.

4. The method of claim 1, further comprising detecting, at the computing device, a sign-out event, wherein the first set of data includes the detected sign-out event.

5. The method of claim 1, further comprising:
    receiving, after the second time and via the first sensor, a second set of data;
    determining, based on the second set of data, that a second interaction session between a second user and the computing device has ended; and
    automatically replacing, at a third time, the second film segment with a third film segment in response to determining the second interaction session has ended.

6. The method of claim 1, wherein the dispensed first film segment is spaced apart from the touchscreen display when the touchscreen display is not in use.

7. A method of providing users of a touch interface projection for a computing device with a sanitary interaction experience, the method comprising:
    automatically dispensing at a first time, in range of a touch interface projector, a first film segment, where the first film segment has a surface area sufficient to serve as a projection surface for the touch interface projection emitted by the touch interface projector;
    receiving, after the first time and via a first sensor associated with the computing device, a first set of data;
    determining, based on at least the first set of data, that a first interaction session between a first user and the computing device has ended; and
    automatically replacing the first film segment with a second film segment in response to determining the first interaction session has ended by retracting the first film segment and dispensing a second film segment.

8. The method of claim 7, wherein the first film segment and the second film segment correspond to two portions of a continuous sheet of film.

9. The method of claim 7, further comprising obtaining the first set of data from a motion sensor located on or near a periphery of the dispensed first film segment.

10. The method of claim 7, further comprising detecting, at the computing device, a sign-out event, wherein the first set of data includes the detected sign-out event.

11. The method of claim 7, wherein the first film segment is opaque.

12. The method of claim 7, further comprising:
    receiving, after the second time and via the first sensor, a second set of data;
    determining, based on the second set of data, that a second interaction session between a second user and the computing device has ended; and
    automatically replacing, at a third time, the second film segment with a third film segment in response to determining the second interaction session has ended.

13. The method of claim 12, further comprising sanitizing the first film segment when the first film segment is retracted, and wherein the third film segment includes the sanitized first film segment.

14. A system for providing users of a touch interface with a sanitary interaction experience, the system comprising a processor and machine-readable media including instructions which, when executed by the processor, cause the processor to:
    cause a first film segment to be dispensed across a touchscreen display at a first time, such that the first film segment extends fully over and covers the touchscreen display;
    receive, after the first time and via a first sensor associated with a computing device connected to the touchscreen, a first set of data;
    determine, based on at least the first set of data, that a first interaction session between a first user and the computing device has ended; and
    cause, at a second time and in response to determining the first interaction session has ended, the first film segment to be replaced with a second film segment.

15. The system of claim 14, wherein the first film segment and the second film segment correspond to two portions of a continuous sheet of film.

16. The system of claim 14, wherein the instructions further cause the processor to obtain the first set of data from a motion sensor located on or near a periphery of the touchscreen display.

17. The system of claim 14, wherein the instructions further cause the processor to detect a sign-out event, and the first set of data includes the detected sign-out event.

18. The system of claim 14, wherein the instructions further cause the processor to:
    receive, after the second time and via the first sensor, a second set of data;
    determine, based on the second set of data, that a second interaction session between a second user and the computing device has ended; and
    cause, at a third time and in response to determining the second interaction session has ended, the second film segment to be replaced with a third film segment.

19. The system of claim 14, wherein the dispensed first film segment is spaced apart from the touchscreen display when the touchscreen display is not in use.

20. The system of claim 14, wherein the first film segment includes a transparent, conductive material.

\* \* \* \* \*